(12) United States Patent
Ruhland et al.

(10) Patent No.: US 6,973,819 B2
(45) Date of Patent: Dec. 13, 2005

(54) DIFFERENTIAL COMPENSATED VAPOR SENSOR

(75) Inventors: Robert M. Ruhland, Shakopee, MN (US); Richard W. Gehman, Freeport, IL (US); Peter M. Anderson, Minneapolis, MN (US); Peter M. Calvagna, Freeport, IL (US)

(73) Assignee: Honeywell International Inc., Morristown, NJ (US)

( * ) Notice: Subject to any disclaimer, the term of this patent is extended or adjusted under 35 U.S.C. 154(b) by 44 days.

(21) Appl. No.: 10/699,188

(22) Filed: Nov. 1, 2003

(65) Prior Publication Data

US 2005/0092066 A1 May 5, 2005

(51) Int. Cl.[7] .................. G01N 33/497; G01N 25/00; G01N 31/12; F23N 5/24
(52) U.S. Cl. .................. 73/23.31; 431/16; 422/94; 73/25.05
(58) Field of Search .................. 73/23.31, 25.01, 73/25.03, 25.05, 1.03; 431/16; 122/14.21; 702/24; 422/94, 95, 96, 97, 98

(56) References Cited

U.S. PATENT DOCUMENTS

| | | | | |
|---|---|---|---|---|
| 4,313,907 A | * | 2/1982 | McNally | 422/97 |
| 4,343,768 A | | 8/1982 | Kimura | |
| 4,356,150 A | | 10/1982 | Johnson et al. | |
| 4,768,947 A | * | 9/1988 | Adachi | 431/80 |
| 5,280,802 A | * | 1/1994 | Comuzie, Jr. | 137/65 |
| 5,386,715 A | | 2/1995 | Evans et al. | |
| 5,401,470 A | * | 3/1995 | Poli | 422/96 |
| 5,948,966 A | * | 9/1999 | Takahashi et al. | 73/23.31 |
| 6,164,958 A | * | 12/2000 | Huang et al. | 431/16 |
| 6,344,174 B1 | * | 2/2002 | Miller et al. | 422/98 |
| 6,390,028 B1 | * | 5/2002 | Langmead et al. | 122/14.2 |
| 6,412,447 B1 | * | 7/2002 | Trant et al. | 122/14.21 |
| 6,622,543 B1 | * | 9/2003 | Ohmi et al. | 73/23.31 |
| 6,807,925 B1 | * | 10/2004 | Lesage | 122/14.1 |
| 2001/0038986 A1 | | 11/2001 | Abraham et al. | |
| 2001/0042564 A1 | | 11/2001 | Abraham et al. | |
| 2003/0180445 A1 | * | 9/2003 | Wang et al. | 427/58 |

OTHER PUBLICATIONS

SmartValve Water Heater Controls, SV9560/SV9570, Honeywell, Inc. 1999, no month.

* cited by examiner

*Primary Examiner*—Michael Cygan
(74) *Attorney, Agent, or Firm*—Kris T. Fredrick; Kermit D. Lopez; Luis M. Ortiz

(57) ABSTRACT

Vapor sensing systems and methods are disclosed. An appliance such as a gas water heater, clothes dryer, and the like can be associated with a controller for controlling the appliance. A vapor sensor is also associated with the appliance, such that the vapor sensor comprises an active sensor and an error sensor, wherein the active sensor generates an active signal and the error sensor generates an error signal. An amplifier is also associated with the vapor sensor, such that the amplifier subtracts the error signal from the active signal to generate a compensated signal indicative of the presence of an ignitable vapor within a vicinity of the appliance and thereby instruct the controller to shut down the appliance.

13 Claims, 4 Drawing Sheets

DIFFERENTIAL COMPENSATED VAPOR SENSOR

TECHNICAL FIELD

Embodiments are generally related to sensing methods and systems. Embodiments are also related to fuel-fired heating appliances, gas-powered water heaters, space heaters, clothes dryers, and the like. Embodiments are also related to vapor sensors for detecting gas vapors. Embodiments are also related to sensors for measuring flow.

BACKGROUND OF THE INVENTION

Fuel-fired heating appliances, such as, for example, gas-fired residential and commercial water heaters, are often formed to include a vertical cylindrical water storage tank with a gas burner disposed in a combustion chamber below the tank. The burner is supplied with fuel gas through a valved gas supply line, and combustion air through an air inlet flow path providing communication between the exterior of the water heater and the interior of the combustion chamber.

Water heaters of this general type are extremely safe and quite reliable in operation. When gasoline or other flammable liquids are stored or used improperly in proximity to the water heater, however, it is possible that flammable vapors may become entrained in the air intake of the water heater. Such vapors might cause secondary combustion to occur within the confines of the water heater combustion chamber. Dangers are equally present with other types of devices, such as hot surface igniters and/or pilot flames. Any source of spark, flame or high temperature (e.g., autoignition temperature devices) can cause fires and/or explosions. If vapors are present, shutting down the ignition system is the most critical response, while shutting down the fuel flow is also desirable.

In residences where appliances such as gas water heaters are located in close proximity to fuel sources, such as gasoline containers, there is a potential for the flammable vapors to be ignited by devices such as a water heater pilot flame. A vapor sensor mounted to the water heater would ideally shut down the pilot if gasoline vapors are detected. Present sensors capable of detecting flammable vapors can be rendered ineffective or deliver false alarms when the sensing element is damaged, exposed to air flow, dust, liquids, oils, or other contaminants.

In view of the foregoing, a continuing need exists for the preclusion of fuel flow to the appliance when extraneous flammable vapors are present exteriorly adjacent the appliance. In particular, a continuing need exists for improved sensors that can sense ignitable gasoline vapors near appliances or devices such as water heaters, clothes dryers, and the like in order to shut them down before they cause fires or explosions. Such vapor sensors should be insensitive (or compensated) for other environmental effects (altitude, humidity, temperatures, etc.) that might cause either false alarms or unsafe conditions.

BRIEF SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

It is, therefore, one aspect of the present invention to provide improved vapor sensor sensing systems and methods.

It is another aspect of the present invention to provide for a differential compensated vapor sensor.

It is yet another aspect of the present invention to provide for an improved vapor sensor, which can be adapted for use with appliances, such as, for example, gas water heaters.

The aforementioned aspects of the invention and other objectives and advantages can now be achieved as described herein. Vapor sensing systems and methods are disclosed herein. In general, an appliance (e.g., gas water heater, clothes dryer, etc.) can be associated with a controller for controlling the appliance. A vapor sensor can be associated with the appliance, wherein the vapor sensor comprises an active sensor and an error sensor, wherein the active sensor generates an active signal and the error sensor generates an error signal.

An amplifier is associated with the vapor sensor, such that the amplifier subtracts the error signal from the active signal to generate a compensated signal indicative of the presence of an ignitable vapor within a vicinity of the appliance and thereby instruct the controller to shut down the appliance. Additionally, an output signal conditioning circuit can be provided, which receives the compensated signal from the amplifier and generates a conditioned signal thereof for transmission to a microprocessor. The microprocessor can instruct the controller to shut down the appliance in response to an input of the conditioned signal to the microprocessor from the amplifier.

The vapor sensor described herein, can also be embodied with devices and appliances other than appliances. For example, the vapor sensor can be embodied with in association with clothes dryers, environmental suits, warning lights in industrial areas, AC electric motors, and any other potential ignition source located in a vapor area. In addition or in lieu of microprocessors, other simpler circuits can be utilized in association with the vapor sensor described herein, such as, for example, comparators, switches, "one-shot" switches, relays, fuses, and the like.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION OF THE INVENTION

The particular values and configurations discussed in these non-limiting examples can be varied and are cited merely to illustrate at least one embodiment of the present invention and are not intended to limit the scope of the invention.

Figure 1:
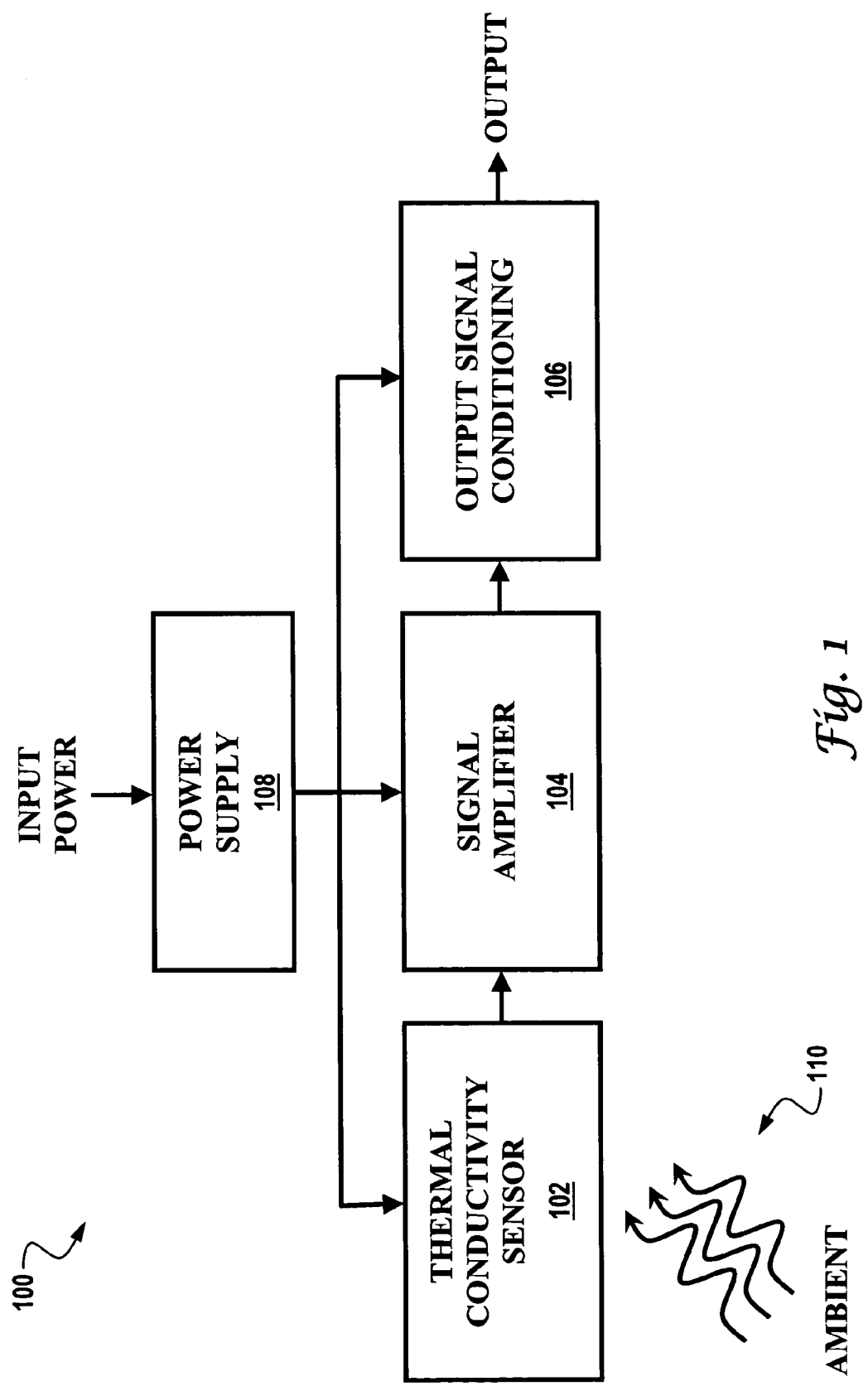
FIG. 1 illustrates a block diagram of a vapor sensing system, which can be implemented in accordance with an embodiment of the present invention.

FIG. 1 illustrates a block diagram of a vapor sensing system 100, which can be implemented in accordance with an embodiment of the present invention. System 100 generally comprises a thermal conductivity sensor 102, which can be adapted for use as a vapor sensor. Vapors which can be detected via system 100 include vapors such as gasoline, carbon dioxide, various alcohols, ammonia, toluene, turpentine, acetone and the like. For illustrative purposes, however, foregoing description is presented with respect to gas water heaters, but is not limited to such devices, but can be embodied with other appliances and devices such as clothes dryers, environmental suits, PLC's in oil refineries, warning lights in industrial areas, and AC electric motors in vapor areas, and the like. Thermal conductivity sensor 102 can measure the amount of power (i.e., voltage or current) required to maintain a self-heated resistor thereof at a specific temperature above ambient temperature, as indicated in FIG. 1 by arrows 110.

The thermal conductivity sensor 102 generates one or more signals that can be input to amplifier 104, which functions as a signal amplifier. Thermal conductivity sensor 102 can generate an error signal and an active signal which are input to amplifier 104. The amplifier 104 subtracts the error signal from the active signal to generate a compensated signal, which is indicative of the presence of an ignitable vapor. Such a compensated signal can then be transmitted to an output signal conditioning circuit 106, which generates a conditioned signal thereof for transmission to a microprocessor (not shown in FIG. 1)

Figure 2:
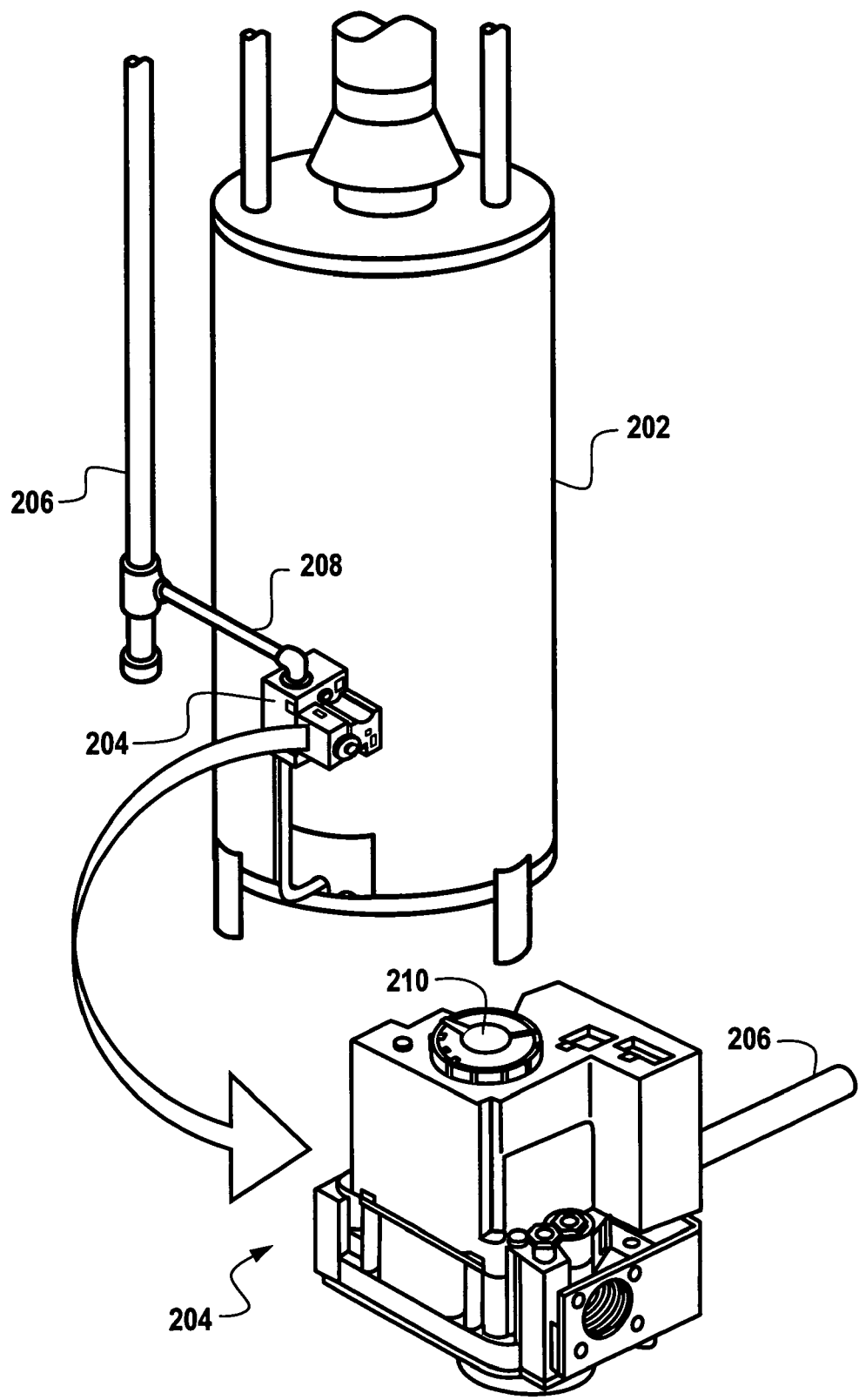
FIG. 2 illustrates a pictorial diagram of a water heater control unit and a water heater, which can be utilized in accordance with an embodiment of the present invention.

FIG. 2 illustrates a pictorial diagram of a water heater control unit 204 and a water heater/tank 202, which can be utilized in accordance with an embodiment of the present invention. Water heater 202 is generally composed of a water tank, to which the control unit 204 can be fastened. A gas line 206 is connected to a control line 208, which in turn is connected to control unit 204. Control unit 204 includes a temperature spud 206 which can be input to water heater 202 (i.e., a water tank) for temperatures sensing capabilities. Additionally, control unit 204 includes an adjustable water heater control knob for adjusting the heat of the water heater 202. It can be appreciated that water heater 202 depicted in FIG. 2 is merely an example of one type of appliance to which embodiments described herein can be adapted.

Water heater 202 is an example of a fuel-fired appliance in which the invention described herein can be embodied. Other types of appliances can be utilized in place of water heater 202, in accordance with alternative embodiments of the present invention, including non-fuel-fired appliances. For example, instead of a water heater 202, devices such as space heaters or clothes dryers can constitute sources of ignitable sparks. Other devices that potentially provide ignitable sparks include devices located in extremely hazardous conditions such as oil refineries, nuclear power plants, explosive manufacturing plants and the like.

Figure 3:
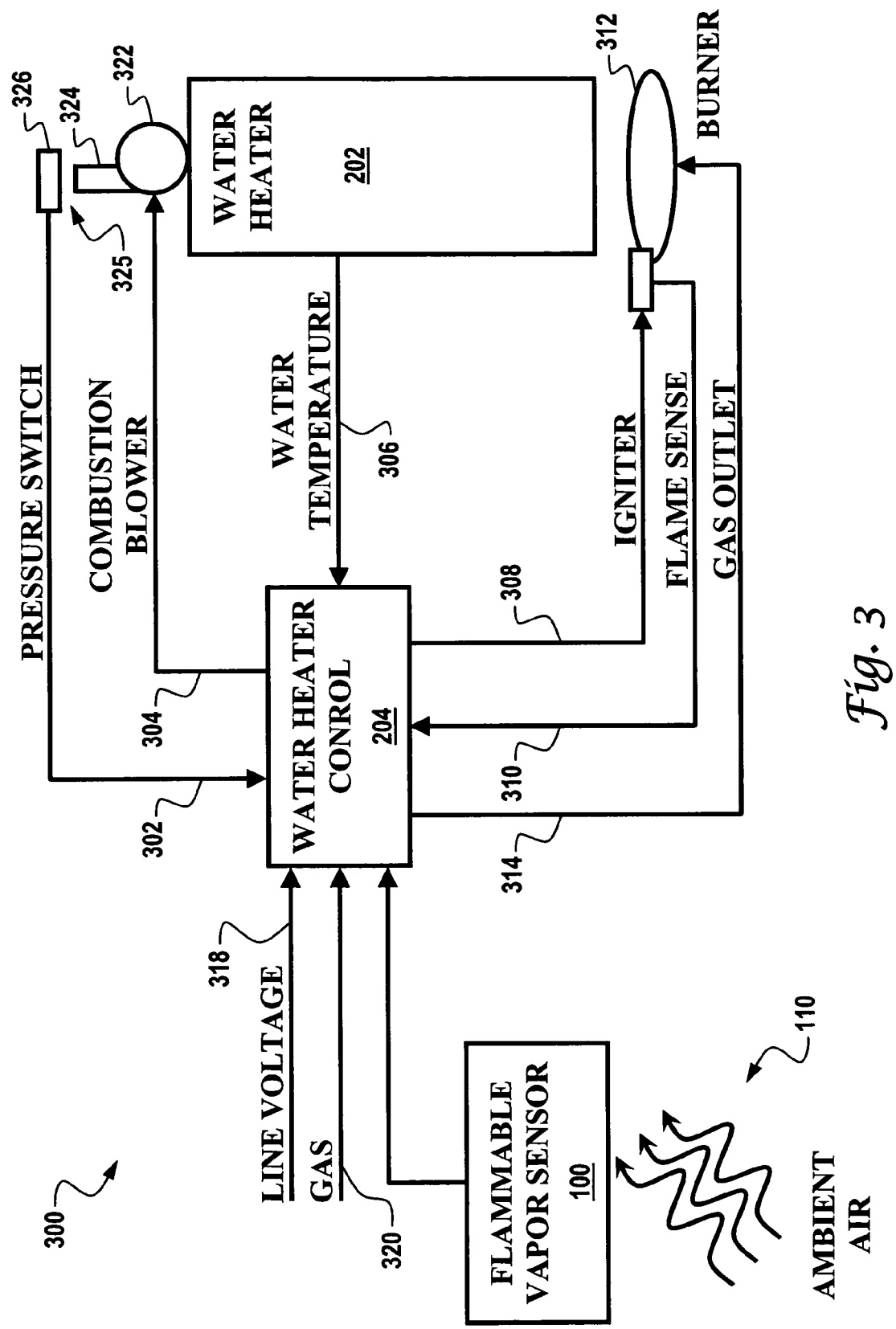
FIG. 3 illustrates a block diagram of vapor sensing system, which can be implemented in accordance with an embodiment of the present invention.

FIG. 3 illustrates a block diagram of vapor sensing system 200, which can be implemented in accordance with an embodiment of the present invention. Note that in FIGS. 1–4 herein, analogous and/or identical parts or elements are generally identified by identical reference numerals. System 300 generally includes a water heater control unit 204, which can receive signals from flammable vapor sensor 100. A gas line 320, which is analogous to gas line 206 and control line 208 of FIG. 2, can be connected to control unit 204, along with a line voltage 318.

A pressure switch 325 can be composed of two switch portions 324 and 326, which provides a pressure switch signal to control unit 204, as indicated by line 302. Additionally, control unit 204 can provide a combustion blower signal to a combustion blower 322, as indicated by line 304. Control unit 204 can also receive a water temperature signal from water heater 202, as indicated by line 306. The temperature of the liquid maintained within water heater 202 can be detected utilizing a temperature detecting device, such as, for example, temperature sensing spud 206 depicted in FIG. 2.

In general, control unit 204 can be utilized to provide high temperature thermal cut-out and gas ignition safety functions, controlling gas flow, ignition source, water temperature and for example, a 120 V ac combustion air blower (e.g., combustion blower 322). Control unit 204 can monitor appliance airflow and switching capabilities to assure proper appliance operation. Control 204 can additionally provide pre-purge, post-purge and timed trial for ignition and multiple ignition trials and auto reset from lockout.

Control unit 204 can additionally provide an igniter signal via line 308 to a burner 312. A gas outlet 314 also extends from control unit 204 to burner 312. The vapor sensor 100 can measure the amount of power (i.e., voltage or current) required to maintain a self-heated resistor thereof at a specific temperature above ambient temperature, as indicated in FIG. 3 by arrows 110. Note that sensor 100 of FIG. 3 is analogous to the vapor sensing system 100 illustrated in FIG. 1

Figure 4:
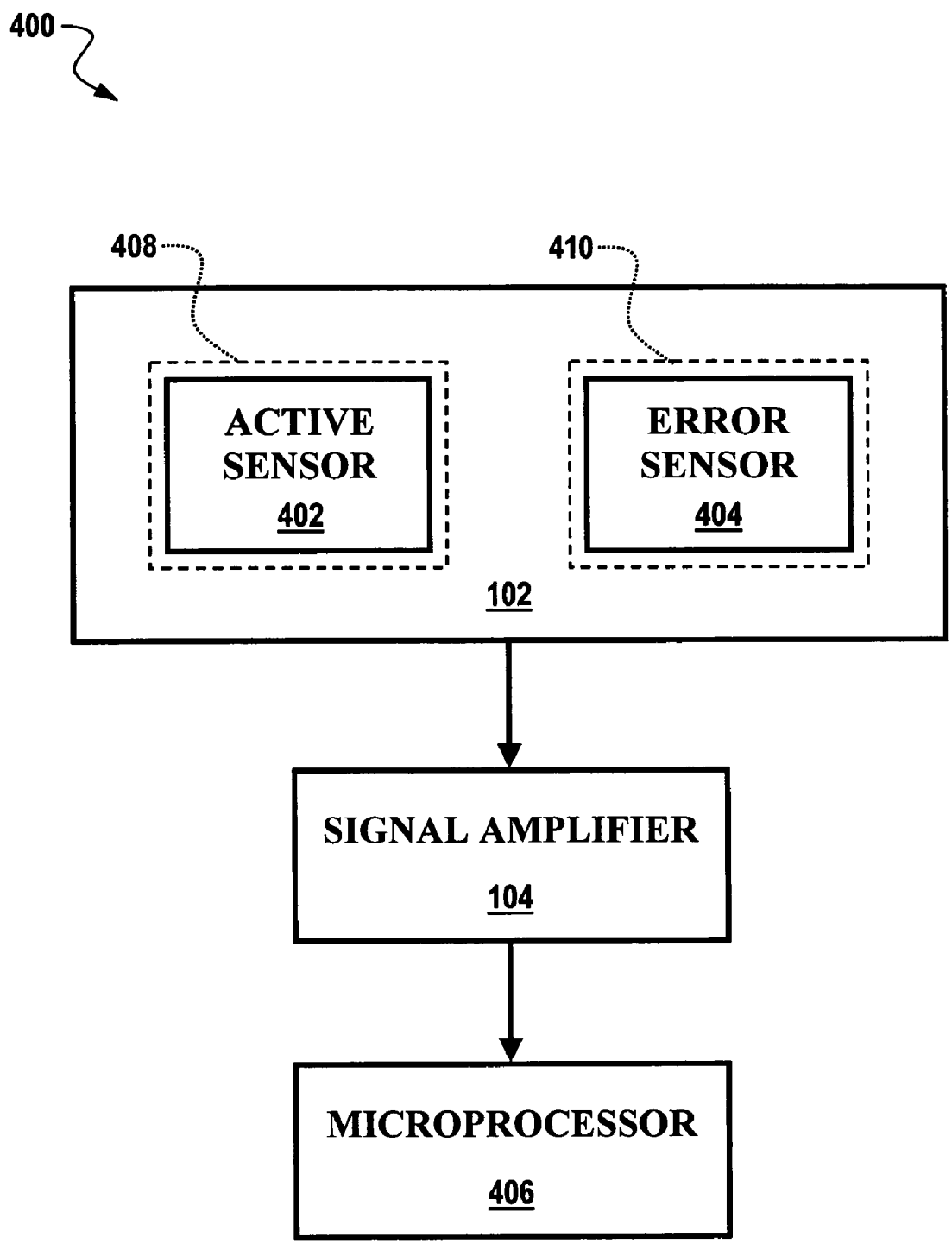
FIG. 4 illustrates a block diagram of a vapor sensing system, which can be implemented in accordance with an alternative embodiment of the present invention.

FIG. 4 illustrates a block diagram of a vapor sensing system 400, which can be implemented in accordance with an alternative embodiment of the present invention. Vapor sensing system 400 generally includes a thermal conductivity sensor 102 (i.e., a vapor sensor), which is composed of an active sensor 402 and an error sensor 404. The active sensor 402 generates an active signal, while the error sensor 404 generates an error signal. The active sensor 402 is exposed to the total atmospheric environment, including fumes, such as, for example, natural gas or gasoline fumes. Border 408 indicates that the active sensor 402 is exposed to the total atmospheric environment.

The error sensor 404, on the other hand, as indicated by border 410, is exposed to everything except fumes, such as natural gas or gasoline fumes. The error signal generated by error sensor 404 can be subtracted from the active sensor signal provided by active sensor 402, thereby providing a compensated signal for the fumes only. The active sensor 402 can be protected from the environment by providing a plastic housing (e.g., border 408) which possesses one side thereof covered by a membrane permeable to all vapors, but impermeable to airflow (e.g., wind), liquids or dust. Border 408 can be configured as such a membrane.

Note that such selectively permeable membranes can be utilized for in association with vapor sensors that detect other types of vapors as well. For example, carbon dioxide, various alcohols, ammonia, toluene, turpentine, acetone and other types of vapors can be detected by the vapor sensor described herein, depending upon the desired embodiment thereof. With regard to fluid flow sensing applications, instead of the two selective membranes described above, the active sensor can be placed into a flow stream and the error sensor exposed to the fluid, but not to the flow. Such an embodiment can be accomplished utilizing the membrane from the active flammable vapor sensor described herein.

The error sensor 404 can be surrounded by a similar protective housing and/or membrane. Such a membrane (i.e., border 410) can selectively pass air and humidity, but not gasoline vapors, while also protecting the error sensor 404 from airflow, liquids, and/or dust. The output of both sensors (i.e., active sensor 402 and error sensor 404) can then be input to an instrumentation amplifier or other control system, such as signal amplifier 104, which can be utilized to subtract the error signal from the active signal. The configuration leaves only a signal for gasoline and/or natural gas fumes, if such fumes are present. The signal can then be converted into a form readable by a microprocessor 406. Such a signal form can be, for example, a frequency output or voltage level (e.g., logic "up" or "down").

It is important to note that the vapor sensor described herein, can also be embodied with devices and appliances other than appliances. For example, the vapor sensor can be embodied with in association with clothes dryers, environmental suits, warning lights in industrial areas, AC electric motors, and any other potential ignition source located in a vapor area. In addition or in lieu of microprocessors, other simpler circuits can be utilized in association with the vapor sensor described herein, such as, for example, comparators, switches, "one-shot" switches, relays, fuses, and the like.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered.

The description as set forth is not intended to be exhaustive or to limit the scope of the invention. Many modifications and variations are possible in light of the above teaching without departing from the scope of the following claims. It is contemplated that the use of the present invention can involve components having different characteristics. It is intended that the scope of the present invention be defined by the claims appended hereto, giving full cognizance to equivalents in all respects.

What is claimed is:

1. A vapor sensing system, comprising:
   an active sensor that generates an active signal and an error sensor that generates an error signal;
   wherein said active sensor and said error sensor together comprise a vapor sensor, wherein said error signal is subtracted from said active signal to generate a compensated signal indicative of the presence of an ignitable vapor;
   an amplifier associated with said vapor sensor, wherein said amplifier subtracts said error signal from said active signal to generate said compensated signal, which is indicative of the presence of said ignitable vapor within a vicinity of an appliance associated with said vapor sensor;
   an output signal conditioning circuit which receives said compensated signal from said amplifier and generates a conditioned signal thereof for transmission to a microprocessor;
   a microprocessor for instructing said controller to shut down said appliance in response to an input of said conditioned signal to said microprocessor from said amplifier; and
   wherein said error sensor is surrounded by a membrane which selectively passes air and humidity, excluding ignitable gasoline vapors, to said error sensor, while protecting said error sensor from airflow, liquids, and dust.

2. The system of claim 1 wherein said appliance comprises a fuel-fired appliance.

3. The vapor sensor of claim 1 wherein said vapor sensor comprises a fluid flow sensor.

4. The system of claim 1 wherein said vapor sensor comprises a thermal conductivity sensor, which measures an amount of power required to maintain a self-heated resistor thereof at a specific temperatures above an ambient temperature thereof.

5. The system of 1 wherein said vapor sensor comprises a thermal conductivity sensor, which measures a temperature change at a constant power required of a self-heated resistor thereof.

6. The system of claim 1 wherein said active sensor is exposed to a total atmospheric environment, including ignitable vapors generated by said appliance, and wherein said error sensor is exposed to a said total atmospheric environment, excluding said ignitable vapors generated by said appliance.

7. The system of claim 1 wherein said active sensor is surrounded by a membrane that is permeable to all vapors, except vapors impermeable to airflow, liquids and dust.

8. A vapor sensing method, comprising the steps of:
   providing an active sensor that generates an active signal;
   providing an error sensor that generates an error signal, wherein said active sensor and said error sensor together comprise a vapor sensor, wherein said error signal is subtracted from said active signal to generate a compensated signal indicative of the presence of an ignitable vapor;
   associating an amplifier with said vapor sensor, wherein said amplifier subtracts said error signal from said active signal to generate said compensated signal, which is indicative of the presence of said ignitable vapor within a vicinity of an appliance associated with said vapor sensor;
   providing an output signal conditioning circuit which receives said compensated signal from said amplifier and generates a conditioned signal thereof for transmission to a microprocessor;
   providing a microprocessor for instructing said controller to shut down said appliance in response to an input of said conditioned signal to said microprocessor from said amplifier;
   exposing said active sensor to a total atmospheric environment, including ignitable vapors generated by said appliance; and
   exposing said error sensor to a said total atmospheric environment, excluding said ignitable vapors generated by said appliance.

9. The method of claim 8 wherein said appliance comprises a fuel-fired appliance.

10. The method of claim 8 wherein said vapor sensor comprises a fluid flow sensor.

11. The method of claim 8 wherein said vapor sensor comprises a thermal conductivity sensor, which measures an amount of power required to maintain a self-heated resistor thereof at a specific temperatures above an ambient temperature thereof.

12. The method of 8 wherein said vapor sensor comprises a thermal conductivity sensor, which measures a temperature change at a constant power required of a self-heated resistor thereof.

13. The method of claim 8 further comprising the step of surrounding said active sensor by a membrane that is permeable to all vapors, except vapors impermeable to airflow, liquids and dust.

* * * * *